United States Patent [19]

Knifton et al.

[11] Patent Number: 5,488,178
[45] Date of Patent: Jan. 30, 1996

[54] DITERTIARY BUTYL PEROXIDE PREPARATION FROM TERTIARY BUTYL HYDROPEROXIDE

[75] Inventors: John F. Knifton; Edward T. Marquis, both of Austin; Pei-Shing E. Dai, Port Arthur, all of Tex.

[73] Assignee: Texaco Chemical Inc., White Plains, N.Y.

[21] Appl. No.: 401,107

[22] Filed: Mar. 8, 1995

[51] Int. Cl.$^6$ ................................................. C07C 409/16
[52] U.S. Cl. ............................................ 568/578; 568/558
[58] Field of Search ...................................... 568/558, 578

[56] References Cited

U.S. PATENT DOCUMENTS

| | | | |
|---|---|---|---|
| 3,474,151 | 10/1969 | Grane | 568/578 |
| 4,740,292 | 4/1988 | Chen et al. | 568/578 |
| 4,810,809 | 3/1989 | Sanderson et al. | 568/578 |
| 4,900,850 | 2/1990 | Sanderson et al. | 568/578 |
| 5,288,919 | 2/1994 | Faraj | 568/578 |
| 5,312,998 | 5/1994 | Liotta, Jr. et al. | 568/578 |
| 5,371,298 | 12/1994 | Pourreau et al. | 568/578 |
| 5,420,357 | 5/1995 | Faraj et al. | 568/578 |

*Primary Examiner*—Werren B. Lone
*Attorney, Agent, or Firm*—James L. Bailey; Kenneth R. Priem; Cynthia L. Hunter

[57] ABSTRACT

Disclosed is a method of selective preparation of ditertiary butyl peroxide from tertiary butyl hydroperoxide and t-butanol which comprises reacting said tertiary butyl hydroperoxide and t-butanol over a solid acid catalyst selected from:

a) an acidic montmorillonite clay;
b) an acidic zeolite selected from the group consisting of dealuminized Y-zeolite and pentasil zeolite;
c) an acidic organic resin; and
d) heteropoly acids supported on an oxide selected from Group III or Group IV.

20 Claims, No Drawings

DITERTIARY BUTYL PEROXIDE PREPARATION FROM TERTIARY BUTYL HYDROPEROXIDE

FIELD OF THE INVENTION

The invention is concerned with the generation of ditertiary butyl peroxide. More particularly the invention relates to the selective generation of di-t-butyl peroxide from t-butyl hydroperoxide (tBHP) plus t-butanol (tBA). Still more particularly, this invention relates to the selective generation of di-t-butyl peroxide from t-butyl hydroperoxide (tBHP) plus t-butanol (tBA) using a series of solid acid catalysts.

BACKGROUND OF THE INVENTION

It is known that ditertiary butyl peroxide is a minor constituent of the reaction product when tertiary butyl hydroperoxide is thermally or catalytically decomposed to form tertiary butyl alcohol. Ditertiary butyl peroxide is a valuable commercial product used, for example, as a high temperature free radical initiator in chemical reactions. U.S. Pat. Nos. 4,810,809 and 4,900,850, to Sanderson et al. disclose methods which can be used to recover purified ditertiary butyl peroxide from a reaction product formed by the thermal or catalytic decomposition of tertiary butyl hydroperoxide.

In "Organic Peroxides" edited by Daniel Swern (Wiley Interscience, a Division of John Wiley & Sons, New York), in Vol II, page 157, it is stated that the metal-ion-catalyzed decomposition of primary hydroperoxide yields mainly alcohols, aldehydes and carboxylic acids.

In U.S. Pat. No. 2,854,487, Quin discloses the hydrogenation of hydrocarbon peroxides in the presence of hydrogen and palladium on activated alumina to provide carbinols.

In U.S. Pat. No. 3,474,151 it is disclosed that tertiary butyl alcohol starts to dehydrate at 450° F. and to decompose at a "rapid rate" at temperatures above 475° F. It was disclosed that residual quantities of hydroperoxide contaminants present in tertiary butyl alcohol could be thermally decomposed by heating the contaminated tertiary butyl alcohol at a temperature of 375° F. to 475° F. for about 1 to 10 minutes.

In U.S. Pat. No. 4,294,999 there is disclosed a process wherein isobutane is oxidized in a pressured reactor in the presence of solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane, U.S. Pat. No. 3,474,151, by heating the tertiary butyl alcohol at 375° to 475° F. for about 1 to 10 minutes. Heating tertiary butyl alcohol containing small amounts of peroxides at high temperatures for even short periods of time to remove the peroxides produces undesirable products such as isobutylene.

In U.S. Pat. No. 4,551,553 to Taylor et al. there is disclosed a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Sanderson et al. disclose the use of a variety of catalysts for the decomposition of tertiary butyl hydroperoxide in a series of U.S. patents, including a catalyst composed of unsupported nickel, copper, chromia and iron (U.S. Pat. No. 4,704,482), a catalyst composed of iron, copper, chromia and cobalt (U.S. Pat. No. 4,705,903), a catalyst composed of a base treated hydrogenation catalyst from Groups VIB or VIIIB of the Periodic Table (U.S. Pat. No. 4,742,179), a catalyst consisting essentially of nickel, copper, chromium and barium (U.S. Pat. No. 4,873,380), a catalyst composed of a metal phthalocyanine promoted with a rhenium compound (U.S. Pat. No. 4,910,349), a catalyst composed of a base promoted metal phthalocyanine compound, (U.S. Pat. No. 4,912,269), a catalyst composed of a soluble ruthenium compound promoted with a bidentate ligand (U.S. Pat. No. 4,912,033), a catalyst composed of a metal porphine such as iron (III) or manganese(III) promoted with an alkyl thiol or an amine, a catalyst composed of an imidazole promoted metal phthalocyanine compound (U.S. Pat. No. 4,912,266), (U.S. Pat. No. 4,922,034), a catalyst composed of a metal phthalocyanine promoted with a thiol and a free radical inhibitor (U.S. Pat. No. 4,922,035), a catalyst composed of a borate promoted metal phthalocyanine, (U.S. Pat. No. 4,922,036) or a catalyst composed of a soluble ruthenium compound and an iron compound such as an acetate, a borate, a bromide, a chloride, a 1,3-propanedionate, a 2-ethylhexanoate, an iodide, a nitrate, a 2,4-pentanedionate, a perchlorate or a sulfate (U.S. Pat. No. 5,025,113).

In U.S. Pat. No. 5,345,009, to Sanderson et al., there is disclosed the conjoint production of tertiary butyl alcohol and ditertiary butyl peroxide from tertiary butyl hydroperoxide.

In U.S. Pat. No. 5,288,919, there is disclosed a process for the preparation of dialkyl peroxide which comprises reacting an alcohol (ROH) or an olefin having the formula

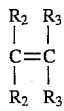

and mixtures in the liquid phase with a hydroperoxide ($R_1OOH$) in the presence of an inorganic heteropoly or isopoly acid catalyst.

A process is described in U.S. Pat. No. 5,312,998, where isobutane oxidate is reacted in the presence of a water soluble acid catalyst. A reaction mixture is formed which is separated into two phases, an aqueous phase and an organic phase which contains the ditertiary butyl peroxide which is subjected to a series of separation steps to recover the product.

It would be desirable if there were an improved method available for selectively generating ditertiary butyl peroxide which demonstrated improved yields of di-t-butyl peroxide and a simpler means of recovery, preferably through the use of a heterogeneous, solid acid catalyst.

SUMMARY OF THE INVENTION

In accordance with the foregoing the novel process of the instant invention for selectively generating di-t-butyl peroxide from t-butylhydroperoxide plus t-butanol comprises bringing said tertiary butyl hydroperoxide charge into contact with a decomposition catalyst comprising a solid acid catalyst selected from the group consisting of:

1) Acidic Clays;
2) Acidic Zeolites;
3) Organic Resins; and
4) Supported heteropoly acids and recovering tertiary butyl alcohol and ditertiary butyl peroxide from the products of said hydroperoxide decomposition reaction.

DESCRIPTION OF THE INVENTION

The method of this invention for selective preparation of di-t-butyl peroxide by decomposition of t-butyl hydroperoxide plus t-butanol in the presence of solid acidic catalysts can be represented by the following equation:

$$t\text{-}C_4H_9OOH + t\text{-}C_4H_9OH \rightarrow t\text{-}C_4H_9OOC_4H_9\text{-}t + H_2O \qquad \text{(Eq. 1)}$$

The tertiary butyl hydroperoxide charge stock may comprise an isobutane oxidation product wherein the tertiary butyl hydroperoxide is dissolved in a mixture of isobutane and tertiary butyl alcohol or may comprise an isobutane oxidation product enriched by the addition of tertiary butyl alcohol, such that the solution of tertiary butyl alcohol in the mixture of isobutane with tertiary butyl alcohol contains from about one to about 80 wt. % of tertiary butyl hydroperoxide.

Alternately, the isobutane reaction product may be charged to a distillation zone where unreacted isobutane is removed as a distillate fraction for recycle to thereby provide a solution of tertiary butyl hydroperoxide in tertiary butyl alcohol containing about one to about 80 wt % of tertiary butyl hydroperoxide.

The catalyst to be used in accordance with the instant invention as a hydroperoxide decomposition catalyst comprises a solid acidic catalyst selected from the group consisting of:

1) Acidic clays, including mineral acid treated clays;
2) Acidic zeolites, including dealuminized Y-zeolite and pentasil zeolite;
3) Organic resins, including perfluorosufonic acid resins; and
4) Heteropoly acids supported on Group III or Group IV oxides, e.g. 12-tungstophosphoric acid on titania.

ACIDIC CLAYS

The acidic clay catalyst comprises an inorganic clay which is acid activated and modified with an acid selected from the group consisting of hydrogen chloride, hydrogen fluoride, fluorosulfonic acids and anhydrides, phosphoric acid, and sulfuric acid, plus combinations thereof. Suitable fluorosulfonic acids or anhydrides include fluorosulfonic acid, trifluoromethanesulfonic acid (triflic acid) and trifluoromethanesulfonic anhydride.

A variety of clay catalysts containing alumina and silica are effective in the subject reaction, however it is necessary that the alumina or silica be acidic under normal operating conditions. A group of catalysts which works well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction of Equation 1 are smectite clays. Smectite clays are discussed in an article in a Chem. Systems Report. (See "Catalysis: Selective Developments" Chem. Systems Report 84-3, 239–249, Section 3.4320). These clays have small particle size and unusual intercalation properties which afford them high surface area. They are alumino silicates with a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

$$M_{x/n}^{n+} \cdot yH_2O(Al_{4-x}Mg_x)(Si_8)O_{20}(OH)_4$$

where M represents the interlamellar, balancing cation (normally sodium or lithium), and x, y and n are integers.

These montmorillonite clays are best used in the present application in an acidic form. Acids activate montmorillonites by attacking and solubilizing structural cations in the octahedral layers. This opens up the clay structure and increases surface area. These acid-treated clays act as strong Bronsted acids. Generally strong mineral acids are used to activate the clay, such as, for example, sulfuric acid and phosphoric acid. As noted in an article by T. Matsuda and E. Kikuchi, titled "Acidic Properties Of Pillared Clays In Relation To Their Catalytic Behavior", in Proceedings of International Symposium on Acid-Base Catalysis, Sapporo, Nov. 28–Dec. 1, 1988, there is an indication Bronsted sites are more active, but have a tendency to convert to Lewis acid sites as temperature increases during calcination of pillared clays. The clays are effective in the form of granules, powders or extrudates.

The acid-treated montmorillonite clays of the present invention upon which the triflic acid or hydrofluoric acid are deposited should have acidities of 1.0 or greater mg KOH/gm, and preferably 5 to 100 mg KOH/gm, titrated to a phenolphthalein end point. Their surface area should be $\geq 30$ m2/g, and preferably 200 to 1000 m$^2$/g. Their moisture content should be limited also, whereby upon heating to 220° F, the weight loss is generally less than 20 wt %, but may be higher under certain circumstances.

Illustrative examples of suitable acidic montmorillonite clays include clays in granular form, such as Engelhard Grade F24, having a 20–60 mesh size, and Grade F24 Superacid Clays. Filtrol Grade F24 is manufactured by Engelhard and has an acid capacity of 16 mg KOH/g. Grade 24 Superacid Clays, also from Engelhard, typically have acidities of 33–93 mg KOH/g. An acid range of about one mg KOH/g to 100 mg KOH/g provides good results, as demonstrated in the Examples.

Where the montmorillonite clay or acid-pretreated montmorillonite clay, as described above, is impregnated with triflic acid or hydrogen fluoride, the clay is generally treated with from 0.01% to 10% triflic acid or HF and preferably the clay is impregnated with from about 0.1% to 2.0% hydrogen fluoride. The instant examples demonstrate that about 0.1% to 2.0% is an effective amount.

Where hydrogen fluoride is deposited on acidic montmorillonite about 0.1% to 2.0% is a preferred effective amount.

An effective amount of triflic acid or hydrogen fluoride would be sufficient to produce an acidity of the catalyst in the range of 1–100 mg KOH/g.

ACIDIC ZEOLITES

The acidic zeolite catalysts which are suitable for the instant invention are selected from the group consisting of dealuminized Y-zeolites and pentasil zeolites.

The preferred catalysts for use in the dealuminated form for the reaction of Eq. 1 are certain crystalline aluminosilicate zeolites, particularly the isostructural group of faujasite zeolites that include the synthetic X- and Y-zeolites. The preferred zeolites for dealumination are the Y-zeolites.

The unit cells of faujasite zeolites are cubic, $a_o \approx 2.5$ nm, and each contains 192 silicon- or aluminum-centered oxygen tetrahedra which are linked through shared oxygen atoms. Because of the net negative charge on each of the aluminum-centered tetrahedra, each unit cell contains an equivalent number of charge-balancing cations. These are exclusively sodium ions in zeolites in their synthesized form. Typical cell contents for the Y-zeolites in the hydrated form are:

$Na_{56}[(AlO_2)_{56}(SiO_2)_{136}]_x \cdot 250\ H_2O$

Y-zeolites are distinguished on the basis of the relative concentration of silicon and aluminum atoms and the consequent effects on detailed structure and related chemical and physical properties. The aluminum atoms in the unit cell of Y-zeolite vary from 76 to 48, resulting in a Si:Al ratio between 1.5 and 3.0. Both the cation concentration and charge density on the aluminosilicate structure are lower for Y-zeolites than for X-zeolites, where the aluminum atoms in the unit cell vary from 96 to 77.

The feature which determines the difference between faujasites and other zeolites built up from sodalite units is the double 6-membered ring or hexagonal prism, by which the units are linked. The sodalite unit, or β-cage, can be represented by a truncated octahedron, with the 24 silicon or aluminum atoms (designated T atoms) taking positions at the vertices. The 36 oxygen atoms are displaced from the midpoints of the edges joining the vertices in order to attain tetrahedral configuration around the T atoms. The free diameter of the void within the β-cage is 0.66 nm, but only the smallest molecules can enter through the 0.22 nm diameter opening in the distorted ring of six oxygen atoms associated with each hexagonal face. Each sodalite unit is linked tetrahedrally across hexagonal faces by six bridging oxygens to four other sodalite units. The larger void spaces enclosed by sodalite units and hexagonal prisms are termed α-cages, or supercages. The s-cage is a 26-hedron with a free diameter of ≈1.3 nm, and it can be entered through four distorted 12-member rings of diameter 0.80–0.90 nm. In this way each α-cage is tetrahedrally joined to four others giving a complex system of void space extending throughout the zeolite structure. The α- and β-cages together give Y-zeolites, along with X-zeolites, the largest void volume of any known zeolites, which is ca. 50 vol % of the dehydrated crystal. From the catalytic viewpoint, the α-cages are by far the most important, since, unlike the β-cages, they permit entry of numerous aliphatic and aromatic compounds.

It has been demonstrated in the instant invention these Y-zeolites are particularly effective in the dealuminated form. Preferably, said Y-zeolites are dealuminated by ammonium exchange followed by calcination, or by treatment with ethylenediaminetetraacetic acid (EDTA) or other chelating agents or by treatment with fluorine or a fluorine-containing compound such as silicon tetrafluoride or ammonium fluorosilicate, or hydrothermal treatment and/or acid treatment. Said dealuminated Y-zeolites should have a silica-to-alumina molar ratio of greater than three, preferably a ratio of 5 or greater and most preferably a silica-to-alumina ratio of 5 to 100. The examples demonstrate the usefulness of a dealuminized Y-zeolite catalyst having a silica-to-alumina ratio of 46.

Examples of suitable commercially available dealuminized Y-zeolites include UOP's LZY-82 and LZY-72, PQ Corporation's CP-304-37 and CP-316-26, UOP's Y-85, Y-84, LZ-10 and LZ-210.

The unit cell size and $SiO_2/Al_2O_3$ molar ratio for typical dealuminated Y-zeolites are noted in the following table:

TABLE 1

| Typical Dealuminized Y-Zeolites | | |
|---|---|---|
| ZEOLITE TYPE | UNIT CELL SIZE, A | $SiO_2/Al_2O_3$ MOLAR |
| LZY-82 | 24.53 | 7.8 |
| LZY-85 | 24.49 | 9.1 |
| LZY-10 | 24.32 | 23.7 |
| LZY-20 | 24.35 | 18.9 |
| LZY-84 | 24.51 | 8.4 |
| LZY-210 | 24.47 | 9.9 |
| LZY-72 | 24.52 | 8.1 |
| CP316-26 | 24.26 | 45.7 |

In another embodiment of the instant invention good results were also realized using the isostructural group of pentasil zeolites.

Molecular sieve zeolites are discussed in "Molecular Sieve Catalysts" by J Ward, Applied Industrial Catalysis, Vol. 3, Ch. 9, p. 271 (1984). Ward provides an overview of the structure of pentasils. These zeolites, as well as silicalite have $SiO_2$-$Al_2O$ ratios greater than 10. Silicalite, ZSM-5, ZSM-11 and related materials have structures with ten-ring channel systems in contrast with the eight-membered zeolites such as A and erionite and the twelve-membered systems such as zeolites X and Y.

Pentasil zeolites are hydrophobic compared with A, X and Y zeolites. ZSM-5 has orthorhombic unit cells, whereas ZSM-11 is tetragonal.

The pentasil structures are very thermal and acid stable. They are synthesized in the presence of ammonium ions, which become an integral part of the structure. Heating up to 600° C. decomposes the organic cations leaving the highly porous structure.

The channel size of pentasil materials is intermediate between, for example, small pore erionite and large pore zeolite Y. Hydrocarbons such as o- and m-xylene, 1,2,4-trimethylbenzene and naphthalene, with minimum diameters of about 6.9Å are absorbed slowly whereas 1,3,5-trimethylbenzene is excluded. Benzene and p-xylene diffuse readily in ZSM-5 whereas larger molecules such as o-xylene diffuse slowly. Highly branched paraffins diffuse much more slowly than normal and monobranched.

Other ZSM series zeolites are not considered to be pentasils. ZSM-21, ZSM-35 and ZSM-38 are considered to be of the ferrierite type zeolite. ZSM-20 is considered of the faujasite type and ZSM-34 is considered to be of the offretite/erionite group. See T. E. Whyte, et al. "Zeolite Advances In The Chemical And Fuel Industries: A Technical Prospective", Catal. Rev. -Sci Eng., 24, (4), 567–598 (1982).

Medium pore, pentasil-type zeolites having 10-membered oxygen ring systems include, for example, ZSM-5, ZSM-11, ZSM-22, ZSM-23, ZSM-48 and laumontite. Their framework structures contain 5-membered oxygen rings and they are more siliceous than previously known zeolites. In many instances these zeolites may be synthesized with a predominance of silicon and with only a very small concentration of other atoms such as aluminum; thus, these zeolites may be considered as "silicates" with framework substitution by small quantities of other elements such as aluminum. Among the zeolites in this group, only ZSM-5 and ZSM-11 have bidirectional intersecting channels, the others have nonintersecting unidirectional channels.

The medium-pore pentasils, unlike other zeolites, have pores of uniform dimension and have no large supercages with smaller size windows. This particular feature is believed to account for their unusually low coke-forming propensity in acid-catalyzed reactions. Because the pentasil zeolites are devoid of the bottle-necks in the window/cage structure, molecules larger than the size of the channel do not form with the exception perhaps at the intersections.

The preferred forms of pentasil zeolite are the highly acidic, high silica forms, having silica-to-alumina mole ratio of at least 30:1, and preferably in the range of 30:1 to 350:1 in the as-synthesized form. A narrower range of 50:1 to 150:1 is preferred and the pentasil zeolites demonstrated in the examples possesses a $SiO_2/Al_2O_3$ ratio of about 140:1.

Generally, it can be said that changes in the Si/Al ratio from one to infinity result in predictable changes in:

Stability, from <700° C. to ~1300° C.

Surface selectivity, from hydrophilic to hydrophobic

Acidity increasing in intrinsic strength

Cation concentration decreasing

Structure from 4-, 6- and 8-rings to 5-rings.

See "Industrial Catalytic Applications of Molecular Sieves" by P. R. Pujadó, et al. In Catal. Today, 13, 113–141 (1992).

The thermal stability of the crystalline lattice of zeolites varies substantially, from about 700° C. for aluminum-rich zeolites, to about 1300° C. for silicalite. Aluminum-rich zeolites are unstable in the presence of acids, while silicon-rich zeolites are stable even in concentrated mineral acids. In contrast, silicon-rich zeolites exhibit low stability in basic solutions. Likewise, aluminum-rich zeolites exhibit a highly-polar hydrophilic surface. Silicon-rich zeolites tend to be more nonpolar and hydrophobic. The onset of hydrophobicity appears to occur at a Si/Al ratio of about 10.

The silica-to-alumina ratio of the zeolite may be determined by the nature of the starting materials used in its preparation and their quantities relative one to another. Some variation in the ratio may therefore be obtained by changing the relative concentration of the silica precursor relative to the alumina precursor, but definite limits in the maximum obtainable silica-to-alumina ratio of the zeolite need be observed. For a pentasil zeolite, this limit is usually about 350:1 (although higher ratios may be obtained) and for ratios above this value, other methods are usually necessary for preparing the desired high silica zeolite. This method generally comprises contacting the zeolite with an acid, preferably a mineral acid such as hydrochloric acid.

Properties of ZSM-5 which are of significance to shape-selective catalysis are the presence of two intersecting channels formed by rings of 10 oxygen atoms. The two intersecting channels, both formed by 10-membered oxygen rings, are slightly different in their pore size. One runs parallel to the a-axis of the unit cell; it is sinusoidal and has a nearly circular (5.4×5.6Å) opening. The other runs parallel to the b-axis and has a straight, but elliptical opening (5.1×5.5Å). See W. M. Meier and D. H. Olson, Atlas of Zeolite Structure Types, International Zeolite Assoc., Polycrystal Book Service, Pittsburgh, 1978.

Said catalysts may be formed in the presence of a binder, such as Group III or Group IV oxide. Group IV oxides used in conjunction with said ZSM-5-zeolite include oxides of aluminum, silicon, titanium, zirconium, hafnium, germanium, tin and lead, as well as combinations thereof. Alumina is preferred. Said binders may comprise 10% to 90% of the formed catalyst.

ACIDIC RESINS

The macroreticular acid cation exchange resins are also useful. The preferred resins are characterized by having a sulfonic acid functionality and an organic polymer matrix.

Any suitable solid acid resin catalyst may be used for this purpose. Suitable resins are typified by the presence of a sulfonic acid groups, e.g., the sulfonated styrene divinyl benzene copolymer exchange resins such as sulfonated cross linked styrene polymers, phenol formaldehyde sulfonic acid resins, benzene-formaldehyde-sulfonic acid resins and the like.

These include resins under the trade names of, for example, AMBERLITE® and AMBERLYST® (Rohm & Haas Co.), DOWEX® (Dow Chemical Co.), PUROLITE® (Purolite CO.), Chempro (Chemical Processing Co.), KATALYSATOR (Bayer A. G.), and the like. The preferred resins are strongly acidic ion exchange resins having acidity capacities of 0.1–6 meg/g. consisting essentially of sulfonated polystyrene, such as a divinyl benzene cross-linked polystyrene matrix containing from about 0.5 to about 20% of copolymerized divinyl benzene. Resins of this nature are manufactured and sold commercially under various trade names such as "Dowex 50", "Nalcite HCR" and AMBERLYST® 15". The use of a catalyst of this type is described, for example, in U.S. Pat. No. 4,144,138 to Rao et al.

Example 2 of the instant invention demonstrates that di-t-butyl peroxide (DTBP) can be prepared from tertiary butyl hydroperoxide (TBHP) plus t-butanol (tBA) using a macroreticular acid resin catalyst, such as Dow's DOWEX® M-31 beads, having an acidity capacity of 4.7 meg/g. Other acid resin catalysts that may be used are Rohm & Haas' AMBERLYST® 15, having an acidity capacity of 4.7 meg/g, AMBERLYST 35 having an acidity capacity of 5.2 meg/g and Dow's DOWEX®monosphere M-31, having a uniform bead size of 500 microns ±50 and an acidity capacity of >4.5 meg/g, as well as AMBERLYST® 18, having an acidity of 5.4 meg/g.

Also effective in the invention of this disclosure are perfluoroinated ion-exchange polymers. These perfluoroinated ion-exchange polymers have fluorocarbon sulfonic acid functionality and the general structure shown below:

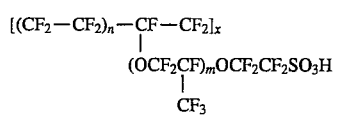

Where m=1, 2, 3 etc. For a more detailed description of super acid supported fluorocarbon sulfonic acid resins see J. D. Weaver et al., Catalysis Today, 14, 195 (1992)

Suitable acidic perfluorinated ion exchange resins include NAFION® NR 50 Beads, from Aldrich Chemical Co., having an acidity capacity of 0.8 meg/g. The application of this resin to the generation of di-t-butyl peroxide from t-butyl hydroperoxide plus t-butanol is illustrated here in Example 4.

SUPPORTED HETEROPOLY ACIDS

The heteropoly acids that are catalysts in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 2:

$$PO_4^{3-} + 12WO_4^{2-} + 27H^+ \rightarrow H_3PW_{12}O_{40} + 12H_2O \qquad (Eq. 2)$$

A wide variety of elements ranging from Group I to Group VIII can become the central atom of the HPA anion, or the heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Equation 2) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table 2.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature (see for example U.S. Pat. No. 3,947,332 (1976).

TABLE 2

Typical Heteropolymolybdate Anions

| CONDENSATION RATIOS | | HETERO ATOMS (X) | CHEMICAL FORMULAS |
|---|---|---|---|
| 1:12 | Keggin structure | $P^{5+}$, $As^{5+}$, $Si^{4+}$, $Ge^{4+}$ | $[X^{n+}Mo_{12}O_{40}]^{-(8-n)}$ |
| | Silverton structure | $Ce^{4+}$, $Th^{4+}$ | $[X^{4+}Mo_{12}O_{42}]^{8-}$ |
| 1:11 | Keggin structure (decomposition) | $P^{5+}$, $As^{5+}$, $Ge^{4+}$, $Si^{4+}$ | $[X^{n+}Mo_{11}O_{39}]^{-(12-n)}$ |
| 2:18 | Dawson structure | $P^{5+}$, $As^{5+}$ | $[X_2^{5+}Mo_{18}O_{62}]^{6-}$ |
| 1:9 | Waugh structure | $Mn^{4+}$, $Ni^{4+}$ | $[X^{4+}Mo_9O_{32}]$ |
| 1:6 | Anderson structure | | |
| | (A type) | $Te^{6+}$, $I^{7+}$ | $[X^{n+}Mo_6O_{24}]^{-(12-n)}$ |
| | (B type) | $Co^{3+}$, $Al^{3+}$, $Cr^{3+}$ | $[X^{n+}Mo_6O_{24}H_6]^{-(6-n)}$ |
| 4:12 | | $As^{5+}$ | $[H_4As_4Mo_{12}O_{52}]^{4-}$ |
| 2:5 | | $P^{5+}$ | $[P_2Mo_5O_{23}]^{6-}$ |

In the case of decomposition of t-butyl hydroperoxide, suitable heterpoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, were X=P or Si, M=Mo or W and n is an integer, 4 or 5.

The preferred heteropoly acids for the practice of this invention include 12-molybdophosphoric acid, $M_3PMo_{12}O_{40}$, 12-tungstophosphoric acid, molybdosilicic acid, $H_4SiMo_{12}O_{40}$ and tungstosilicic acid. Said acids are generally used as their hydrates; they may be employed by themselves, partially or completely dissolved in the feed, or they may be employed as heterogeneous catalysts bonded to a suitable support.

The support should preferably comprise an inert compound. Compounds which may be employed are those containing elements of Group III and IV of the periodic table, such as those discussed above under B-zeolite.

The inert support may be in the form of powders, pellets, spheres, shapes and extrudates. The examples described herein demonstrate the advantages of using extrudates. An extrudate which works well is HSA titania carrier extrudate from Norton Company, ⅛" extrudates with a surface area of 50–100 m²/g.

The weight percent of heteropoly acid to Group III/Group IV support should be such that the concentration of the polyatom (Mo, W, Nb or V) in the formulated catalyst is in the range of 0.1 wt % to 30 wt %. Concentrations outside this range may also be employed. Where the heteropoly acid is, for example, 12-molybdophosphoric acid, supported on titania, a suitable quantity of molybdenum is 1–10 wt %. In the preparation of a tungstophosphoric acid-on-titania catalyst, on the other hand, the tungsten content may be 1–30 wt %.

The method of the instant invention may be conducted batchwise in kettles or by continuously passing the reactants through a tubular reactor.

The catalytic decomposition of tertiary butyl hydroperoxide is preferably conducted at a temperature within the range of about 20° to about 160° C. and, preferably, at a temperature within the range of about 600° to about 120° C. The reaction is preferably conducted at a pressure sufficient to keep the reactant and the reaction products in liquid phase. A pressure of about atmospheric to about 10,000 psi is desirable.

Flow rates of the charge solution to the reaction zone should be adjusted in order to provide an appropriate contact time within the reactor. In a batch process, the holding time may suitably be from about 0.1 to 100 hours, and preferably about 1 to 10 hours.

The t-butyl hydroperoxide may be a byproduct of the oxidation of isobutane, along with unreacted isobutane, tertiary butyl alcohol, and oxygen-containing by-products, which is then used as the charge stock of the instant invention. The concentration of tertiary butyl hydroperoxide in the charge stock can be one to 80 wt %.

As indicated, the catalytic decomposition of the tertiary butyl hydroperoxide may suitably be conducted at a temperature within the range of about 20° to about 160° C., preferably from about 60° to about 120° C., and most preferably from about 80° C. to 100° C. at autogenous pressure or, if desired, at a super atmospheric pressure up to 10,000 psig for a contact time within the range of about 0.1 to about 100 hours, preferably about 1 to 10 hours.

When the process is practiced in a continuous manner by continuously charging the tertiary butyl hydroperoxide charge stock to a reactor containing a fixed bed of pelleted hydroperoxide decomposition catalyst, the space velocity is suitably in the range of about 0.1 to about 10 volumes of tertiary butyl hydroperoxide charge stock per volume of catalyst per hour. Preferably, the space velocity is within the range of about 1 to about 2 volumes of tertiary butyl hydroperoxide charge stock per volume of catalyst per hour.

The following examples illustrate:

1. The synthesis of ditertiary butyl peroxide from tBHP using a mineral acid treated montmorillonite clay (Example 1).

2. The preparation of ditertiary butyl peroxide using a series of solid acid catalysts (Table 3, Examples 2–8), including:

Sulfonic Acid Resins (Dowex M-31)

Pentasil Zeolites (ZSM-5)

Perfluorosulfonic Acid Resins (NAFION NR 50)

Dealuminized Y-zeolites (CP 316-26)

HF Treated Clays (0.6%–1.6% HF, mineral acid treated clays)

3. The generation of DTBP using a 12-Tungstophosphoric acid-on-titania (Example 9).

EXAMPLE 1

This example illustrates the synthesis of di-t-butyl peroxide from t-butyl hydroperoxide via acidic clay catalysis.

To a 300 cc capacity, stainless steel batch reactor, fitted with temperature, pressure controls, and a mechanical stirrer, was charged 50g of isobutane oxidate comprising 50% t-butyl hydroperoxide (277 m mole) and 50% t-butanol (337 m mole) plus 50 g of t-butanol (675 m mole) and 20 g of acidified montmorillonite clay granules clay Grade F24 20/60 mesh, acidity 16 mg KOH/g). The mixture was flushed with nitrogen, pressured to 50 psi with nitrogen, with stirring then heated to 80° C. for 4 hours, with continued stirring.

Upon cooling, the recovered product mix was weighed (114g), filtered to remove used clay catalyst, and the liquid filtrate analyzed by g/c and gc-ms techniques.

Typical product composition was as follows:

| | |
|---|---|
| t-Butanol | 70.3% |
| Di-t-butylperoxide | 14.3% |
| t-Butylhydroperoxide | 12.7% |
| Isobutylene | 1.5% |

EXAMPLES 2–8

These examples illustrate the synthesis of di-t-butylperoxide from t-butylhydroperoxide via catalysis by a series of acidic clays, zeolites, resins, etc.

Following the procedures and using the equipment of Example 1, the subject synthesis was effected using the following catalysts:

A sulfonic acid resin (DOWEX® M-31 beads, acidity 4.7 meg/g).

A pentasil, ZSM-5, zeolite (silica/alumina ratio 140, powder).

A fluorosulfonic acid resin (NAFION® NR 50 beads, 10/35 mesh, acidity 0.8 meg/g).

a dealuminized Y-zeolite (CP 316-26, $SiO_2/Al_2O_3$ ratio 46, powder).

A 0.6% HF treated acidic clay.

A 1.3% HF treated acidic clay.

A 1.6% HF-treated, high crystallinity (HC) clay.

The results of these synthesis are summarized in Table 3, where the abbreviations are: Isobutylene ($C_4H_8$), t-butanol (tBA), di-t-butylperoxide (DTBP) and t-butylhydroperoxide (TBHP).

TABLE 3

Di-t-Butylperoxide from t-Butylhydroperoxide

| Example | Catalyst | Product Composition % | | | | TBHP Conv. (%) |
|---|---|---|---|---|---|---|
| | | $C_4H_8$ | tBA | DTBP | TBHP | |
| 2 | DOMEX ® M-31 | 2.3 | 63.9 | 15.1 | 17.7 | 29 |
| 3 | ZSM-5 | 2.6 | 71.2 | 0.2 | 24.7 | <2 |
| 4 | NAFION NR 50 | 1.8 | 57.0 | 32.1 | 6.9 | 72 |

TABLE 3-continued

Di-t-Butylperoxide from t-Butylhydroperoxide

| Example | Catalyst | Product Composition % | | | | TBHP Conv. (%) |
|---|---|---|---|---|---|---|
| | | $C_4H_8$ | tBA | DTBP | TBHP | |
| 5 | CP 316-26 | 0.3 | 77.3 | 3.9 | 17.2 | 31 |
| 6 | 0.6% HF-Clay | 4.4 | 70.1 | 14.0 | 6.5 | 74 |
| 7 | 1.3% HF-Clay | 2.0 | 75.0 | 7.8 | 11.5 | 52 |
| 8 | 1.6% HF-HC Clay | 3.0 | 74.4 | 9.8 | 8.4 | 65 |

EXAMPLE 9

This Example illustrates the synthesis of di-t-butylperoxide from t-butylhydroperoxide using a 12-tungstophosphoric acid-on-titania catalyst.

Following the procedures and using the equipment of Example 1, the reactor was charged with 50g of isobutane oxidate (50% t-butylhydroperoxide and 50% t-butanol), plus 50 g of t-butanol and 20 g of 12 tungstophosphoric-acid-on-titania catalyst (16.7% tungsten on ⅛" titania, powdered, prepared by the method described in U.S. Pat. No. 4,683, 335). The mixture was flushed with nitrogen, pressured to 50 psi with nitrogen, with stirring, then heated to 80° C., for 4 hours, with continued stirring.

Upon cooling, the recovered product mix was weighed (113 g), filtered to remove used clay catalyst and the liquid filtrate analyzed by glc and gc-ms techniques.

Typical product composition was as follows:

| | |
|---|---|
| t-Butanol | 52.1% |
| Di-t-butylperoxide | 25.6% |
| t-Butylhydroperoxide | 9.5% |
| Isobutylene | 9.1% |

Estimated t-butylhydroperoxide Conversion 62%

What is claimed is:

1. A method for selectively generating ditertiary butyl peroxide which comprises bringing a solution of tertiary butyl hydroperoxide charge stock in tertiary butyl alcohol into contact with a catalytically effective amount of a solid acid catalyst comprising an acidic montmorillonite clay in a reaction zone in a liquid phase under hydroperoxide conversion conditions including a temperature within the range of about 20° C. to 160° C. and a pressure of about atm to 10,000 psig, selectively generating ditertiary butyl peroxide, along with t-butanol, from tertiary butyl hydroperoxide, and recovering said ditertiary butyl peroxide product.

2. The method of claim 1 wherein the charge stock contains from one to 80 wt % tertiary butyl hydroperoxide and the conversion conditions include a temperature of from about 60° C. to 120° C.

3. The method of claim 1 wherein the space velocity in the reaction zone is in the range of about 0.1 to about 10 volumes of tertiary butyl hydroperoxide charge stock per volume of catalyst per hour.

4. The method of claim 1 wherein the catalyst comprises a montmorillonite clay having the structure

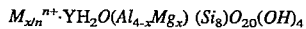

where m represents the interlamellar, balancing cation (normally sodium or lithium), and x, y and n are integers and the clay is acidic from pretreatment with an acid selected from the group consisting of hydrogen fluoride, hydrogen chloride, fluorosulfonic acids or anhydrides, or mineral acids, as well as combinations thereof.

5. The method of claim 4 wherein the clay is treated with hydrogen fluoride.

6. The method of claim 5 wherein the acidity of the hydrogen fluoride treated clay is in the range of 1 to 100 mg KOH/g.

7. A method for selectively generating ditertiary butyl peroxide which comprises bringing a solution of tertiary butyl hydroperoxide charge stock in tertiary butyl alcohol into contact with a catalytically effective amount of a solid acid catalyst comprising an acidic zeolite selected from a dealuminized Y-zeolite and a pentasil zeolite in a reaction zone in a liquid phase under hydroperoxide conversion conditions including a temperature within the range of about 20° C. to 160° C. and a pressure of about atm to 10,000 psig, selectively generating ditertiary butyl peroxide, along with t-butanol from tertiary butyl hydroperoxide, and recovering said ditertiary butyl peroxide product.

8. The method of claim 7 wherein the catalyst is a Y-zeolite dealuminized in a manner selected from:

a) ammonium exchanging the Y-zeolite followed by calcination;
   b) by treating with ethylenediaminetetraacetic acid.
   c) treating the Y-zeolite with a fluorine-containing compound from the group consisting of silicon tetrafluoride and ammonium fluorosilicate; or
   d) treating the Y-zeolite with steam alone or followed by acid treatment.

9. The method of claim 8 wherein the dealuminized Y-zeolite has a silica-to-alumina molar ratio of 5 to 100.

10. The method of claim 7 wherein the acidic catalyst is a pentasil zeolite having a silica:alumina ratio of 30:1 to 350:1.

11. A method for selectively generating ditertiary butyl peroxide which comprises bringing a solution of tertiary butyl hydroperoxide charge stock in tertiary butyl alcohol into contact with a catalytically effective amount of a solid acid catalyst comprising an acidic organic polymer resin in a reaction zone in a liquid phase under hydroperoxide conversion conditions including a temperature within the range of about 20° C. to 160° C. and a pressure of about atm to 10,000 psig, selectively generating ditertiary butyl peroxide, along with t-butanol, from tertiary butyl hydroperoxide, and recovering said ditertiary butyl peroxide product.

12. The method of claim 11 wherein the organic polymer acid resin is a solid, divinyl benzene cross-linked sulfonated polystyrene resin.

13. The method of claim 12 wherein the said sulfonated polystyrene resin has an acidity capacity of 0.1 to 6 meg/g.

14. The method of claim 12 wherein the acid resin is a perfluorinated ion-exchange polymer.

15. The method of claim 14 wherein the perfluorinated ion-exchange polymer has the general structure:

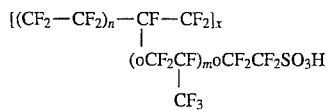

where n=1,2,3 etc.

16. A method for selectively generating ditertiary butyl peroxide which comprises bringing a solution of tertiary butyl hydroperoxide charge stock in tertiary butyl alcohol into contact with a catalytically effective amount of solid acid catalyst comprising a heteropoly acid having the Keggin structure represented by $H_{8-n}[XM_{12}O_{40}]$ where x=P or Si, M=Mo or W and n is an integer which is 4 or 5, supported on an inert support comprising an oxide selected from the group consisting of oxides of titanium, aluminum, silicon and zirconium, in a reaction zone in a liquid phase under hydroperoxide conversion conditions including a temperature within the range of about 20° C. to 160° C. and a pressure of about atm to 10,000 psig, selectively generating ditertiary butyl peroxide, along with t-butanol, from tertiary butyl hydroperoxide and recovering said ditertiary butyl peroxide product.

17. The method of claim 16 wherein the oxide support is titania.

18. The method of claim 16 wherein the heteropoly acid is selected from the group consisting of 12-tungstophosphoric acid, and 12-molybdophosphoric acid, 12-tungstosilicic acid and 12-molybdosilicic acid.

19. The method of claim 18 wherein the heteropoly acid is 12-tungstosphoric acid and the oxide support is titania.

20. The method of claim 19 wherein the 12-tungstophosphoric acid-on-titania catalyst has a tungsten content of 1–30wt. %.

* * * * *